(12) United States Patent
Pindiprolu et al.

(10) Patent No.: US 8,347,693 B2
(45) Date of Patent: Jan. 8, 2013

(54) APPARATUS AND METHODS FOR CONTINUOUS COMPATIBILITY TESTING OF SUBTERRANEAN FLUIDS AND THEIR COMPOSITIONS UNDER WELLBORE CONDITIONS

(75) Inventors: Sairam K S Pindiprolu, Pune (IN); Dennis Willie Gray, Comanche, OK (US); Christopher Lynn Gordon, Pune (IN); Balasundaram Balaraman, Pune (IN)

(73) Assignee: Halliburton Energy Services, Inc., Houston, TX (US)

( * ) Notice: Subject to any disclaimer, the term of this patent is extended or adjusted under 35 U.S.C. 154(b) by 336 days.

(21) Appl. No.: 12/869,447

(22) Filed: Aug. 26, 2010

(65) Prior Publication Data
US 2012/0048008 A1 Mar. 1, 2012

(51) Int. Cl.
*G01N 11/14* (2006.01)
*G01N 11/16* (2006.01)

(52) U.S. Cl. ............ 73/54.32; 73/54.01; 73/54.23; 73/54.28

(58) Field of Classification Search .......... 73/53.01, 73/53.05, 54.01–54.03, 54.23–54.43
See application file for complete search history.

(56) References Cited

U.S. PATENT DOCUMENTS

| | | | | | |
|---|---|---|---|---|---|
| 1,817,739 | A | * | 8/1931 | Dintilhac | 73/54.28 |
| 2,096,222 | A | * | 10/1937 | Bock | 73/54.35 |
| 2,142,854 | A | * | 1/1939 | La Pierre | 73/54.25 |
| 2,354,923 | A | * | 8/1944 | Mcnamee | 73/54.28 |
| 2,358,374 | A | * | 9/1944 | Ashcraft | 73/32 A |
| 2,360,546 | A | * | 10/1944 | Cardwell, Jr | 73/32 R |
| 2,468,370 | A | * | 4/1949 | Kalle | 73/54.31 |
| 2,550,052 | A | * | 4/1951 | Fay | 73/54.26 |
| 2,563,567 | A | * | 8/1951 | Wakefield | 73/54.32 |
| 2,626,786 | A | | 1/1953 | McGlothin | |
| 2,633,016 | A | * | 3/1953 | Millington | 73/54.25 |
| 2,703,006 | A | * | 3/1955 | Savins | 73/54.33 |
| 3,062,040 | A | * | 11/1962 | McKennell et al. | 73/54.24 |
| 3,269,171 | A | | 8/1966 | Bruss et al. | |
| 3,282,091 | A | * | 11/1966 | Webb | 73/54.33 |
| 3,535,914 | A | * | 10/1970 | Mehrbrodt et al. | 374/46 |
| 3,572,086 | A | * | 3/1971 | Johnston | 3/54.32 |

(Continued)

OTHER PUBLICATIONS

ANSI, API and ISO, "Recommended Practice for Testing Well Cements", ANSI/API Recommended Practice 10B-2 / ISO 10426-2, 2005, pp. 1-171, API Publishing Services, Washington, D.C., USA.

(Continued)

*Primary Examiner* — David Rogers
(74) *Attorney, Agent, or Firm* — Booth Albanesi Schroeder LLC; John Wustenberg; John F. Booth (57) ABSTRACT

Disclosed is a fluid testing device which utilizes a small, cross-section fluid interface to separate a test fluid chamber from a drive and measuring chamber. The test fluid chamber contains the test fluid and a paddle-type fluid test assembly. The drive and measuring chamber contains a second fluid and assemblies for moving the paddle and for determining the resistance movement. The two chambers are connected together by a narrow cross-section passageway allowing for continuous testing while test fluids are flowed through the test chamber and for successive testing of different samples without breaking down the device between tests. A pair of coaxial shafts extends between the test fluid chamber and the drive and measuring chamber. The shafts are connected together by a spring located in the drive chamber whereby the resistance to movement is determined by measuring the deflection in the spring. The shafts are magnetically coupled to a motor to rotate the shafts.

18 Claims, 9 Drawing Sheets

U.S. PATENT DOCUMENTS

| | | | | |
|---|---|---|---|---|
| 3,751,975 | A * | 8/1973 | Katsura | 73/54.38 |
| 3,935,726 | A * | 2/1976 | Heinz | 73/54.35 |
| 4,283,938 | A | 8/1981 | Epper et al. | |
| 4,466,276 | A * | 8/1984 | Ruyak et al. | 73/54.35 |
| 4,524,611 | A * | 6/1985 | Richon et al. | 73/54.35 |
| 4,630,468 | A * | 12/1986 | Sweet | 73/54.43 |
| 4,633,708 | A * | 1/1987 | Blommaert | 73/54.35 |
| 4,653,313 | A | 3/1987 | Sabins et al. | |
| 4,668,911 | A * | 5/1987 | Mueller et al. | 324/207.18 |
| 4,736,624 | A * | 4/1988 | Arnstein et al. | 73/54.35 |
| 4,823,594 | A * | 4/1989 | Gray | 73/54.01 |
| 4,864,849 | A * | 9/1989 | Wright | 73/54.31 |
| 4,884,577 | A * | 12/1989 | Merrill | 600/370 |
| 5,025,656 | A * | 6/1991 | Wright | 73/32 A |
| 5,052,219 | A * | 10/1991 | Fery et al. | 73/152.22 |
| 5,287,732 | A * | 2/1994 | Sekiguchi | 73/54.33 |
| 5,301,541 | A * | 4/1994 | Joseph et al. | 73/54.32 |
| 5,315,864 | A * | 5/1994 | Surjaatmadja et al. | 73/54.32 |
| 5,394,739 | A * | 3/1995 | Garvey et al. | 73/54.23 |
| 5,531,102 | A | 7/1996 | Brookfield et al. | |
| 5,535,619 | A * | 7/1996 | Brookfield | 73/54.33 |
| 5,770,795 | A * | 6/1998 | Behar et al. | 73/54.23 |
| 5,799,734 | A | 9/1998 | Norman et al. | |
| 5,874,665 | A * | 2/1999 | Larsson | 73/54.28 |
| 6,112,581 | A * | 9/2000 | Scheider et al. | 73/54.24 |
| 6,167,752 | B1 * | 1/2001 | Raffer | 73/54.28 |
| 6,257,051 | B1 * | 7/2001 | Boyle et al. | 73/54.01 |
| 6,412,338 | B2 * | 7/2002 | Boyle et al. | 73/54.34 |
| 6,450,013 | B1 * | 9/2002 | Gallagher | 73/54.25 |
| 6,582,116 | B2 * | 6/2003 | Nielsen | 366/279 |
| 6,584,831 | B1 * | 7/2003 | Kasameyer et al. | 73/54.23 |
| 6,708,554 | B2 * | 3/2004 | Hettwer et al. | 73/54.43 |
| 6,782,735 | B2 | 8/2004 | Walters et al. | |
| 6,782,753 | B1 | 8/2004 | Immer et al. | |
| 6,817,223 | B2 * | 11/2004 | Lenz | 73/10 |
| 6,874,353 | B2 | 4/2005 | Johnson et al. | |
| 6,938,464 | B1 * | 9/2005 | Bi | 73/54.28 |
| 6,951,127 | B1 | 10/2005 | Bi | |
| 6,997,045 | B2 | 2/2006 | Wallevik et al. | |
| 7,017,393 | B2 * | 3/2006 | Doe et al. | 73/54.28 |
| 7,074,364 | B2 * | 7/2006 | Jähn et al. | 422/62 |
| 7,275,419 | B2 * | 10/2007 | Raffer | 73/54.28 |
| 7,287,416 | B1 * | 10/2007 | Bi | 73/54.28 |
| 7,392,842 | B2 | 7/2008 | Morgan | |
| 7,407,631 | B2 * | 8/2008 | Swon et al. | 422/561 |
| 7,412,877 | B1 * | 8/2008 | Bi | 73/54.28 |
| 8,132,445 | B2 * | 3/2012 | Laun et al. | 73/54.28 |
| 8,230,723 | B2 * | 7/2012 | Moon et al. | 73/54.28 |
| 2003/0192366 | A1 * | 10/2003 | Taylor | 73/54.32 |
| 2004/0149019 | A1 * | 8/2004 | Johnson et al. | 73/54.28 |
| 2005/0238540 | A1 * | 10/2005 | Swon et al. | 422/99 |
| 2007/0012441 | A1 | 1/2007 | Heathman et al. | |
| 2008/0083268 | A1 * | 4/2008 | Hammami et al. | 73/54.01 |
| 2008/0163703 | A1 | 7/2008 | Boncan et al. | |
| 2009/0056423 | A1 * | 3/2009 | Franck et al. | 73/54.35 |
| 2009/0188312 | A1 | 7/2009 | Sears et al. | |
| 2010/0071442 | A1 * | 3/2010 | Moon et al. | 73/54.28 |
| 2010/0116034 | A1 * | 5/2010 | Abbott et al. | 73/54.35 |
| 2010/0181070 | A1 * | 7/2010 | Harris et al. | 166/280.1 |
| 2011/0061451 | A1 * | 3/2011 | Harris et al. | 73/54.42 |

OTHER PUBLICATIONS

D.L. Lord, Helical Screw Rheometer: A New Tool for Stimulation Fluid Evaluation, SPE 18213, 1998.

D.L. Lord, et al. Real-Time Fracturing Fluid Rheology Measurements With the Helical Screw Rheometer, SPE 19734, 1989.

A. Thesing, New Device for Rheology Measurements of Proppant-Laden Fluids With the Fann 50 Viscometer, SPE 58759, 2000.

Specification for Cements and Materials for Well Cementing, ASI Specification 10A, 23rd Edition, April 2002.

API Specification 10A/IS) 10426-1, Specification for Cements and Materials for Well Cementing, 23rd Edition, Addendum 1, Jan. 2005.

Model 35 Viscometer Instruction Manual, Fann Instrument Company, 2008.

* cited by examiner

APPARATUS AND METHODS FOR CONTINUOUS COMPATIBILITY TESTING OF SUBTERRANEAN FLUIDS AND THEIR COMPOSITIONS UNDER WELLBORE CONDITIONS

BACKGROUND

1. Technical Field

The invention relates to testing apparatus and methods for conducting tests of compatibility on wellbore fluids and their contaminated mixtures and slurries under specific pressure and temperature conditions and, in particular, apparatus and methods for testing fluid mixtures and slurries for use in subterranean wellbores under simulated wellbore conditions.

2. Background Art

When drilling, completing, and treating subterranean hydrocarbon wells, it is common to inject materials fluid form with complex structures, such as, suspensions, dispersions, emulsions and slurries. These injected materials are present in the wellbore with materials such as water, hydrocarbons and other materials originating in the subterranean formations. The materials present in the wellbore will be referred to herein as "wellbore fluids" or "wellbore liquids". These substances and their mixtures flow rather than plastically deform. The flow of these fluids and mixtures cannot be characterized by a single value, instead the apparent viscosity and shear stress changes due to other factors such as temperature and pressure and the presence of other materials. Indeed, the materials in some mixtures may be characterized as incompatible. Two fluids are incompatible if undesirable physical and/or chemical interactions occur when the fluids are mixed. Many times incompatibility is characterized by apparent viscosity and shear stress. When apparent viscosity of A+B is greater than apparent viscosity of A as well as apparent viscosity of B, they are said to be incompatible at the tested shear rate.

Cement is routinely inserted to block or seal off fluid flow, isolate hydrocarbon zones and provide support for well casings. Wellbores typically are at elevated temperatures and pressures and contain contaminating fluids and solids. The flow characteristics of various cement mixtures can be tested in the presence of a contaminant, such as, a fluid spacer or drilling mud. In addition, mixtures of spacer fluids and drilling mud can be tested. Other examples, including mixtures of wellbore fluids pumped into the wellbore to carry particulate in suspension to the hydrocarbon bearing formations, are located outside the wellbore.

It is common to determine optimum wellbore liquids and incompatibility of those liquids in a laboratory by running a series of tests of different liquid mixtures under wellbore conditions. Testing various ratios of mixtures of wellbore liquids is done to replicate the changes in the wellbore concentrations of the fluids. These wellbore liquids and mixtures that have variable viscosity are sometimes called "Non-Newtonian fluids." Testing a series of samples of actual wellbore mixtures during well treatment is also common. Viscosity, elasticity, shear stress, and consistency are rheological characteristics that need to be measured for a given fluid or mixture.

Known devices used to test fluids for these characteristics include viscometers, rheometers and consistometer. Testing comprises filling a test chamber with a first mixture, bringing the chamber to pressure and temperature test conditions, and then conducting tests of the fluids characteristics. In prior art devices the successive test of different mixture ratios requires emptying and refilling the test chamber with a different mixture to repeat the test.

SUMMARY OF THE INVENTIONS

The present inventions provide equipment and procedures for successively and accurately testing the compatibility of a series of wellbore fluids, fluid mixtures and fluid slurries in the presence of contaminants and under pressure and temperature conditions existing in the well.

BRIEF DESCRIPTION OF THE DRAWINGS

The drawing is incorporated into and forms a part of the specification to illustrate at least one embodiment and example of the present invention. Together with the written description, the drawing serves to explain the principles of the invention. The drawing is only for the purpose of illustrating at least one preferred example of at least one embodiment of the invention and is not to be construed as limiting the invention to only the illustrated and described example or examples. The various advantages and features of the various embodiments of the present invention will be apparent from a consideration of the drawing in which.

DETAILED DESCRIPTION

The present invention provides an improved testing apparatus and method for successively testing a variety of combinations of fluid and solid based additives for use in subterranean hydrocarbon wells. The present invention's particular applicability is to the testing of various proportional mixtures of drilling mud and fluid spacers and, in addition, the testing of various proportional mixtures of drilling mud, fluid spacers and cement.

Figure 1:
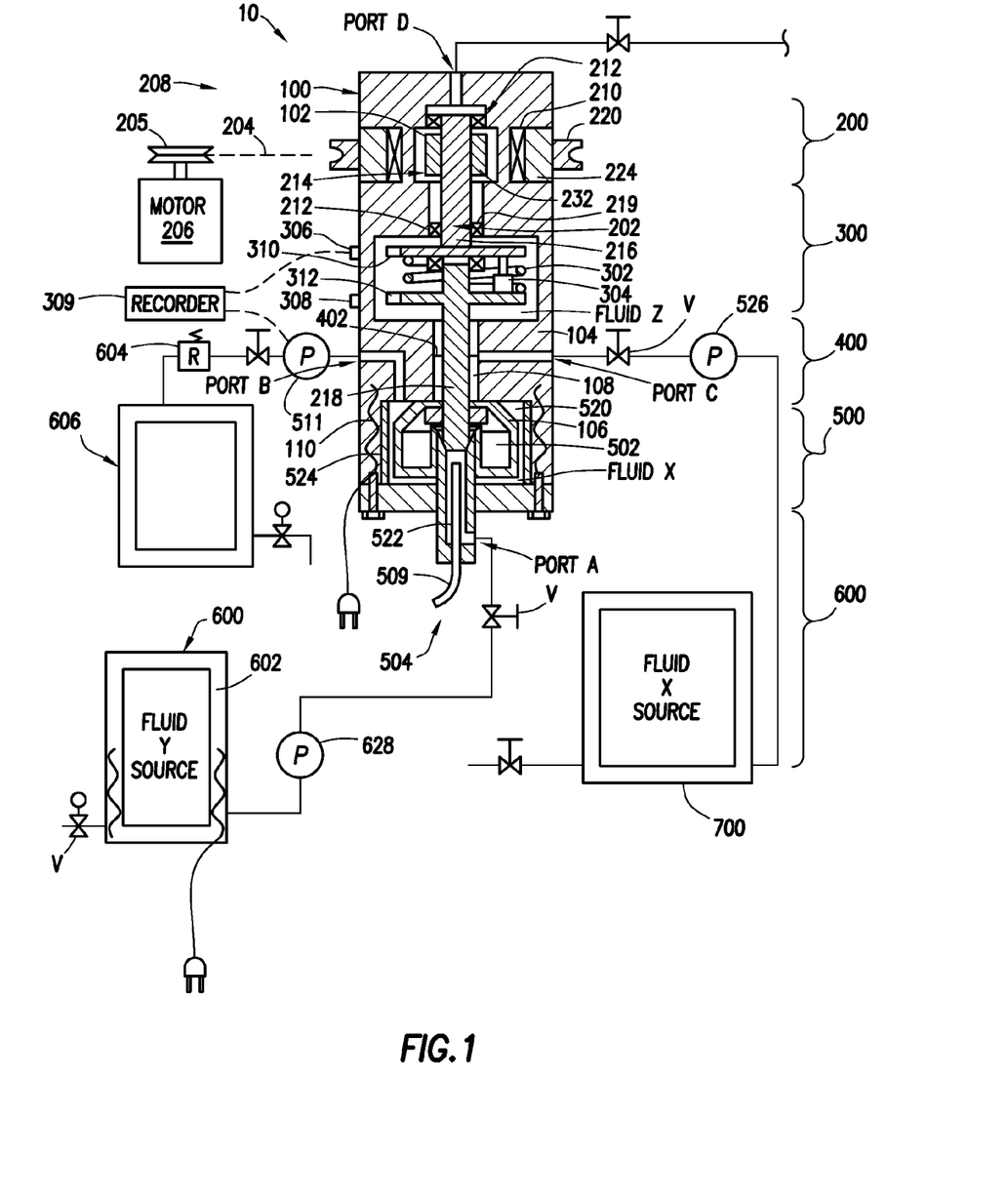
FIG. 1 is a diagram of the testing apparatus system of the present invention illustrated in longitudinal section.

Referring more particularly to the drawings, wherein like reference characters are used throughout the various figures to refer to like or corresponding parts, there is shown in FIG. 1 one embodiment of the testing apparatus 10 of the present invention. The testing apparatus 10 is a pressure vessel designed to withstand test pressures and temperatures. The testing apparatus 10 can be described as basically comprising a pressure chamber housing assembly 100, a magnetic drive assembly 200, a torque spring assembly 300, a fluid interface assembly 400 and a hot well or sample testing assembly 500.

The pressure chamber housing assembly 100 is designed to test a liquid or slurry mixture in an enclosed pressure chamber 102. The housing is designed to be used in controlled temperature and pressure tests up to subterranean hydrocarbon wellbore operating temperatures as high as about 600° F. and pressures as high as about 50,000 psi. In FIG. 1, the housing is illustrated as a single piece pressure vessel, however, it is envisioned that considerations of manufacturing and assembly would require multiple pieces or sections such as is illustrated in the other embodiments described herein. In this particular embodiment the housing is shown with five external ports in fluid communication with the interior of the enclosed pressure chamber 102. These ports are identified for description by letters A-E. Note that Port E is illustrated in FIG. 5b but is not shown in the section forming FIG. 1.

The enclosed pressure chamber 102 is somewhat hourglass shaped with an upper chamber portion 104 and a lower chamber portion 106 connected together by a relatively reduced or smaller cross-section area or passageway 108. As can be seen in this embodiment the reduced cross section is a passageway. In any case the reduced cross section portion has a maximum cross-section area which is less than the maximum cross-section area of the first and second chambers. The magnetic drive assembly 200 and torque spring assembly 300 are located in the upper chamber portion 104. The hot well or sample testing assembly 500 is located in the lower chamber portion 106. As will be described in more detail hereinafter the fluid interface assembly 400 is located in the passageway 108.

Generally, the magnetic drive assembly 200 comprises an embodiment of a drive means for rotating the shaft extending into hot well or sample testing assembly 500. The magnetic drive assembly 200 transfers power into the pressure chamber 102 to rotate shaft assembly 202. The shaft assembly 202 in this embodiment is illustrated as being located entirely inside the enclosed pressure chamber 102 and therefore eliminates the need for a rotating seal through the housing wall. A motor sprocket drive assembly 208 is connected by sprocket 205 and an endless belt 204 to mag drive sprocket 220 on magnetic drive assembly 200. The sprocket assembly 208 includes permanent magnets and is rotationally supported from the upper end of the pressure chamber housing assembly 100 by bearings 210.

The shaft assembly 202 comprises an upper portion 216 and lower portion 218 connected together by a resilient member such as a spring. The shaft portions in this embodiment comprise two rigid metallic members, however, it is envisioned that the shaft portions could comprise more than two portions and need not be formed from metallic materials. The shaft assembly 202 is supported in the upper chamber portion 104 by a pair of bearings 212 which in this embodiment a simple cylindrical bushing. Bearing 212 allows the shaft to rotate about a vertical axis. A magnetic follower assembly 214 is carried on the upper end of the shaft assembly 202 adjacent to the sprocket assembly 208. The magnetic follower assembly 214 contains permanent magnets which are coupled by magnetic forces to the sprocket assembly 208. It can be seen that as the motor 206 causes the external magnets 224 in the sprocket drive assembly 208 to rotate about the upper end of the pressure chamber housing assembly 100, the magnets in the magnetic follower assembly 214 will cause the shaft assembly 202 to rotate about a vertical axis.

By using this magnetic coupling to drive or rotate the shaft assembly 202 the necessity of mounting the shaft to extend through the wall of the pressure chamber housing assembly 100 is eliminated. When testing at extremely high wellbore pressure, it is difficult to control leakage around a shaft extending through rotating seals without applying drag forces to the shaft. It has been found that drive means having seals associated with a through housing shaft mounting can induce error into the torsion measurements; however, in some testing situations seal induced error is not significant. Accordingly, alternative drive means for rotating the shaft could be used in place of the illustrated embodiment. For example, electro magnets could be mounted on the shaft and/or around the housing. As previously described a drive means with a shaft extending through enclosure wall could be used. In the illustrated embodiment, the shaft assembly 202 will be described as divided into an upper shaft portion 216 and a lower shaft portion 218. It is appreciated that one or any number of shaft portions could be used.

In the illustrated embodiment, a torsion spring assembly 300 is used as a means to measure drag or the resistance to rotation encountered by the shaft during rotation. In the present embodiment, the shaft upper 216 and shaft lower 218 portions of the shaft assembly 202 are connected together by a spring 302 in the torque spring assembly 300. Alternatively, instead of torsion springs Cantilevered Pivot Bearings could be used such as those obtained from Riverhawk Company, New Hartford, N.Y.

The shaft upper portion 216 extends upward and is connected and rotated by the magnetic follower assembly 214. The shaft lower portion 218 extends down from the upper chamber portion 104 through the fluid interface 402 of the fluid interface assembly 400 and into the lower chamber portion 106 of the hot well or sample testing assembly 500. The shaft upper portion 216 extends into a bearing 219 mounted on the shaft upper portion 216.

Test sample contacting rotating paddle assembly 502 are connected to the lower shaft portion 218 and when moved or rotated through the test sample encounter drag or shear forces caused by the test sample contacting the paddles 502. As used herein, the term "paddle" is defined generically as any member without any particular shape or size moved in contact with the test fluid to incur a drag or shear force as it moves. An example of another a paddle shape is a cylinder rotated about its axis in the test fluid. In this embodiment the removable cylindrical cup 524 lines the lower chamber portion 106. In addition, removable vanes 520 are mounted to removable cylindrical cup 524 to interact with the rotating paddle assembly 502. In this embodiment the paddles, vanes and cup are removable for ease in cleaning.

The torque spring assembly 300 connects the shaft upper and lower portions 216 and 218 together by torsion spring 302. If during operation (rotation of the upper shaft portion 216) drag is incurred by the lower shaft portion 218, the torsion spring 302 will allow relative rotation between the lower and upper portions in proportion to the magnitude of resistance encountered. Stop assembly 304 limits rotational deflection of the spring 302 to less than 360 degrees. As will be described, the magnitude of the drag is measured and utilized to determine the characteristics of the fluid being tested in the hot well or sample testing assembly 500. In the illustrated embodiment, magnets 310 and 312 are connected to the shaft upper portion 216 and shaft lower portion 218, respectively. Transducers 306 and 308 sense the relative position of magnets as they rotate from which the resistance can be determined. As will be explained the transducers can be connected to a recorder processor 309 to store or convert the transducer outputs to usable data.

Alternative to the torsion spring 302, a torsion measuring means could be used which could include a strain gauge on the shaft. It should be appreciated that the resistance to rotation caused by contacting the test sample can be measured by alternative torsion measuring means located external to the pressure chamber housing assembly 100, in which case the torsion spring assembly is eliminated. For example, the load or torque on the motor can be determined from dynamic electrical measurements of the motor. Alternatively, a torsion measuring assembly can be connected to the magnetic drive assembly or motor. However, the preferred embodiment uses a torsion spring immediately adjacent to the paddle.

When a sample fluid or mixture is being tested in the hot well or sample testing assembly 500, the drag or resistance encountered by the sample contacting paddles 502 will be proportional to the shear stress at the rotational speed being tested of the sample. A temperature sensing assembly 504 such as a thermocouple 509 is located inside the pressure chamber housing assembly 100 preferably in contact with the fluid located in the lower chamber portion 106 and centered in the paddle assembly to eliminate drag errors caused by fluid contact with the thermocouple 509. In addition, a pressure sensing assembly 511 is provided to measure the pressure of the fluid inside the pressure chamber housing assembly 100.

Example A

An example of a method of utilizing the test apparatus 10 will be described in reference to FIG. 1 and is illustrative of the present invention used to test a variety of proportional mixtures of test fluids and/or solids X and Y. Hydrocarbon well application examples of components of mixtures to be tested include hydrocarbon liquids and gases, acids, gels, cement, mud, proppant, sand, bauxite spacers and elastomers, clays, slag, fly ash, surfactant, polymers and the like. For example, slurries of proppant from 8 to 100 mesh can be tested. In this example, two fluids in liquid form are tested, however, a variety of proportional mixtures and slurries of two or more fluids and solids could also be tested. Indeed a single fluid could also be tested under different conditions using the present inventions.

The first step in this example is to manipulate the valves v and pump 526 to inject fluid X from reservoir assembly 700 into the lower chamber portion 106 through Port C. Injection of fluid X continues until it is discharged from open Port B indicating that the lower chamber portion 106 of the hot well or sample testing assembly 500 is filled with fluid X and Fluid X is in contact with paddles 502. Alternatively, Fluid X could be injected through Port A into the lower chamber 106 until discharge is observed at Ports B and C.

Next, Ports B and C are closed and pressurizing fluid Z is pumped into either Port E (See FIG. 5b) or Port C until discharge is observed at the Port D. This discharge indicates that gas has been displaced from the upper chamber portion 104 and the upper chamber portion has been filled with fluid. Fluid Z is preferably a liquid that is insoluble and immiscible in fluids X and Y. Fluid Z can be an inert lubricating/pressurizing fluid such as nonflammable mineral oil or the like.

Pumping fluid Z to fill the upper chamber portion 104 will create a fluid interface 402 at the vertical height Port C intersects the passageway 108. Fluid interface 402 as used herein means the boundary area where the fluids in the upper and lower chambers are in contact with each other. In this example, it is where fluids X and Z are in contact. Port D is then closed and the fluids contained in the testing apparatus 10 are brought to the desired testing temperature using the electrical heating elements 110 and desired testing pressure using a pump connected to the Port D or E.

While fluid X is being brought to the desired testing temperature and pressure, the motor 206 is activated to rotate the rotating paddle assembly 502. To monitor the temperature, a thermocouple 509 is located in chamber 522 with its output connected to the recorder 309. Also, a pressure sensing assembly 511 is connected to the recorder to monitor the pressure of the test fluid. However, the motor could be activated before the testing temperature and pressure are reached. Drag on the rotating paddle assembly 502 contacting the test liquids (and mixtures) will cause torque in the shaft and relative rotation between shaft upper portion 216 and shaft lower portion 218 as torsion spring 302 flexes. Transducers 306 and 308 will sense (measure) the relative rotation between the upper shaft portion 216 and lower shaft portion 218. The relative rotation is relational to the apparent viscosity or shear stress of the sample contacting rotating paddle assembly 502 once calibrated.

To test the mixture of fluids X and Y, a measured amount of fluid Y is pumped from a reservoir assembly 600 through Port A and into chamber 522 the hot well or sample testing assembly 500 while an equal amount is discharged from Port B into the waste reservoir 606. Preferably, an adjustable back pressure regulator 604 is connected to Port B set to maintain the testing pressure during the adding step. It is important to note that in this and the following examples the fluid interface 402 located in the passageway 108 is not disturbed by the controlled injection and the discharge of fluid. Preferably the fluid Y in reservoir assembly 600 has been preheated and maintained at the testing temperature, so that the resultant mixture of fluids X and Y can be quickly tested at the desired test temperature. Preferably the motor 206 is off during the pumping fluid Y into the test chamber.

The process performing a series of tests of different mixtures containing progressively higher proportions of fluid Y can be accomplished by utilizing Port A and B and pump 628 to add and remove additional amounts of fluid Y and mixtures of fluids X and Y while pressure regulator 604 maintains pressure in the chamber 106. It is to be noted that the addition of fluid Y can be accomplished by maintaining the fluid interface 402 undisturbed in the passageway 108. By utilizing this method a plurality of successive tests can be performed without the necessity of emptying the chamber in the sample testing assembly and without removing and replacing the lubrication/pressurizing fluid Z. It should be appreciated that a variety of types of mixtures and slurries can be tested utilizing the apparatus and methods of the present inventions described herein.

Figure 8A:
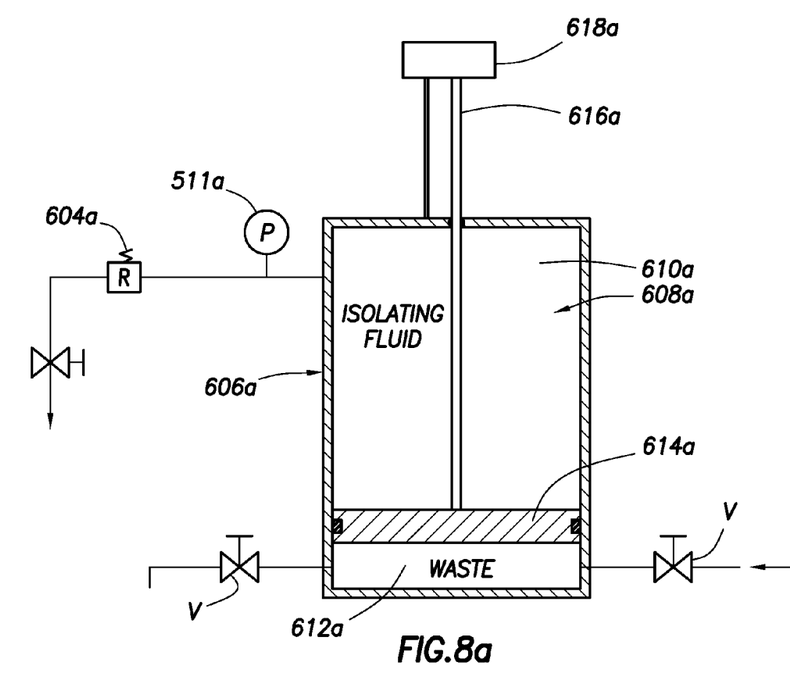
FIGS. 8a and 8b are diagrams of alternative embodiments of the fluid waste and source reservoirs of FIG. 1.

Alternatively, as illustrated in FIG. 8a, the pressure sensing assembly 511a and regulator 604a could be located on the discharge side of the waste reservoir 606a. In addition, chamber 608a is divided into variable volume sub chambers 610a and 612a by piston 614a. Chamber 610a is filled with an inert or isolating liquid such as mineral oil and is displaced from the chamber 610a as liquid is pumped from hot well assembly 500 and into chamber 614a, it is noted that the regulator 604a and pressure sensor 511a are in contact with the isolating liquid rather than the Fluids X and Y. This protects these devices from any damaging fluids being tested. In this embodiment piston 614a has a rod 616a that extends through the wall of reservoir 606a and is connected to a linear volume detector 618a. Alternatively, the rod extending through the reservoir wall could be eliminated and an inferno sensor could be used to measure the piston's movement. For example, a linear magnetic displacement sensor could be used. The output of detector 618a can be connected to recorder 528 to record the volume of Fluids X and Y pumped.

Figure 8B:
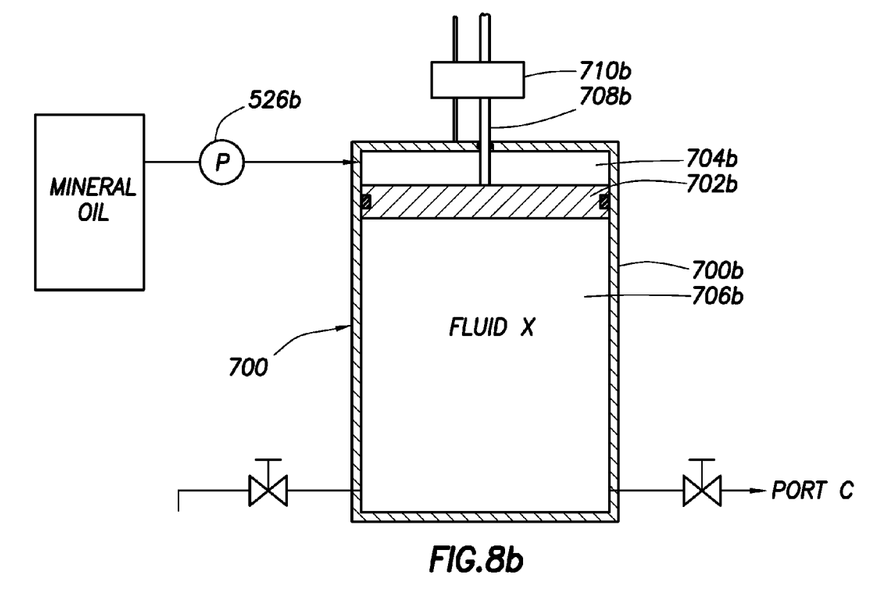

As illustrated in FIG. 8b, an alternative embodiment for isolating the pump 526b from the test fluids. In this embodiment fluid reservoir 700b is assembled with a piston 702b separates reservoir 700b into two chambers 704b and 706b. An isolating liquid such as mineral oil is pumped into chamber 702b by pump 526b to displace Fluid X from chamber 706b and into hot well assembly 500. A piston rod 708a is connected to linear detector 710b. Preferably the detector 618a and 710b are "LVDT" which can be obtained from Novotechnik U.S., Inc. of Southborough, Mass. or RDP Electrosense, Inc. of Pottstown, Pa.

Example B

The testing apparatus can also be used to perform a series of tests of samples of well fluids. In this example, the reservoir assembly 600 is connected to a source of well fluids such as, for example, the drilling mud which at the time was being circulated through the well. As in example A, the ports are used to place a first test sample in the lower chamber portion 106. As described in Example "A" using the ports, a suitable second fluid is placed above the test fluid and the contents of the enclosure are brought to test conditions. The test fluid is then tested. When it is desired to test a second test sample, the second sample is pumped into the lower chamber portion 106 by displacing the first sample and to discharge it from the apparatus into waste reservoir 606. The fluids remaining in the lower chamber 106 will approach, but not completely reach, a 100% concentration of the second sample. The second sample is then tested. This process can be repeated with succession of different samples. Alternatively, a first test sample can be tested as described and thereafter different proportions of the second fluid added to the sample in chamber 106 and tested successively.

Example C

The apparatus can also be used to perform continuous monitoring (testing) of a fluid as it is pumped through the lower chamber portion by pump 526. For example, a fluid being pumped into or circulated through a wellbore (or other fluid application) could be continuously sampled and the sample pumped through the lower chamber. With the motor running, the shear forces are constantly measured and recorded along with the temperature and pressure. Ideally, a pressure regulator 604 is connected to the discharge port to maintain the test pressure while the test fluid is being circulated through the lower chamber.

After the test is completed the lower chamber portion 106 is disassembled and the removable cylindrical cup 524, vanes 520 and rotating paddle assembly 502 are removed and cleaned.

Figure 2:
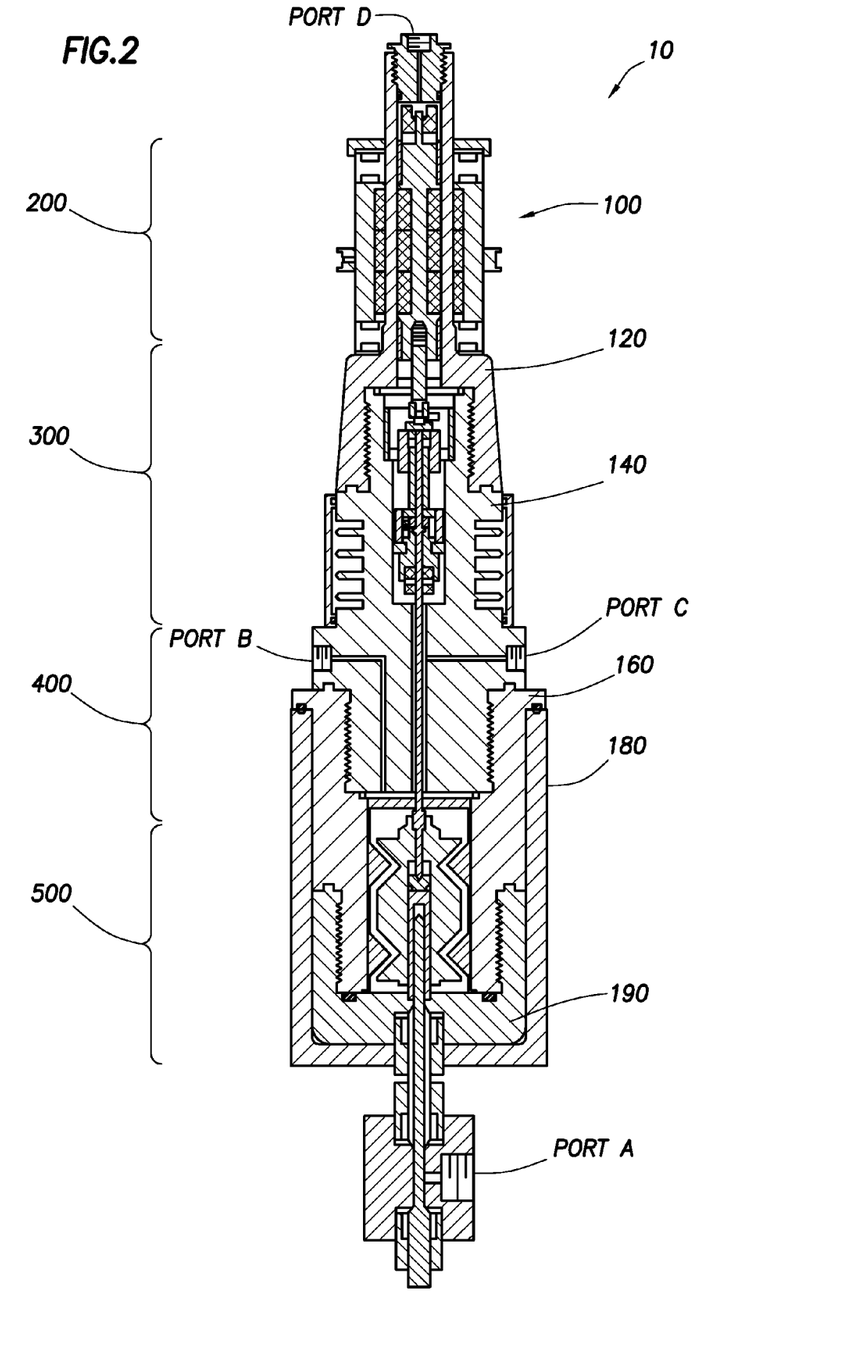
FIG. 2 is a partial section view of another embodiment of the testing apparatus of the present invention.

Turning now to FIG. 2, the details of another embodiment of the testing apparatus 10 will be described. In this embodiment, the pressure chamber housing assembly 100 is made up of an upper subassembly 120, a middle subassembly 140, a lower subassembly 160, a bottom cover 180 and an internal bottom cap 190. The adjacent subassemblies are connected together in sealed engagement to form the enclosed pressure chamber 102. The upper subassembly 120 houses the magnetic drive assembly 200. The middle subassembly 140 houses the torque spring assembly 300 and the fluid interface assembly 400. The lower subassembly 160, bottom cover and internal bottom cap 190 house the hot well or sample testing assembly 500.

Figure 3:
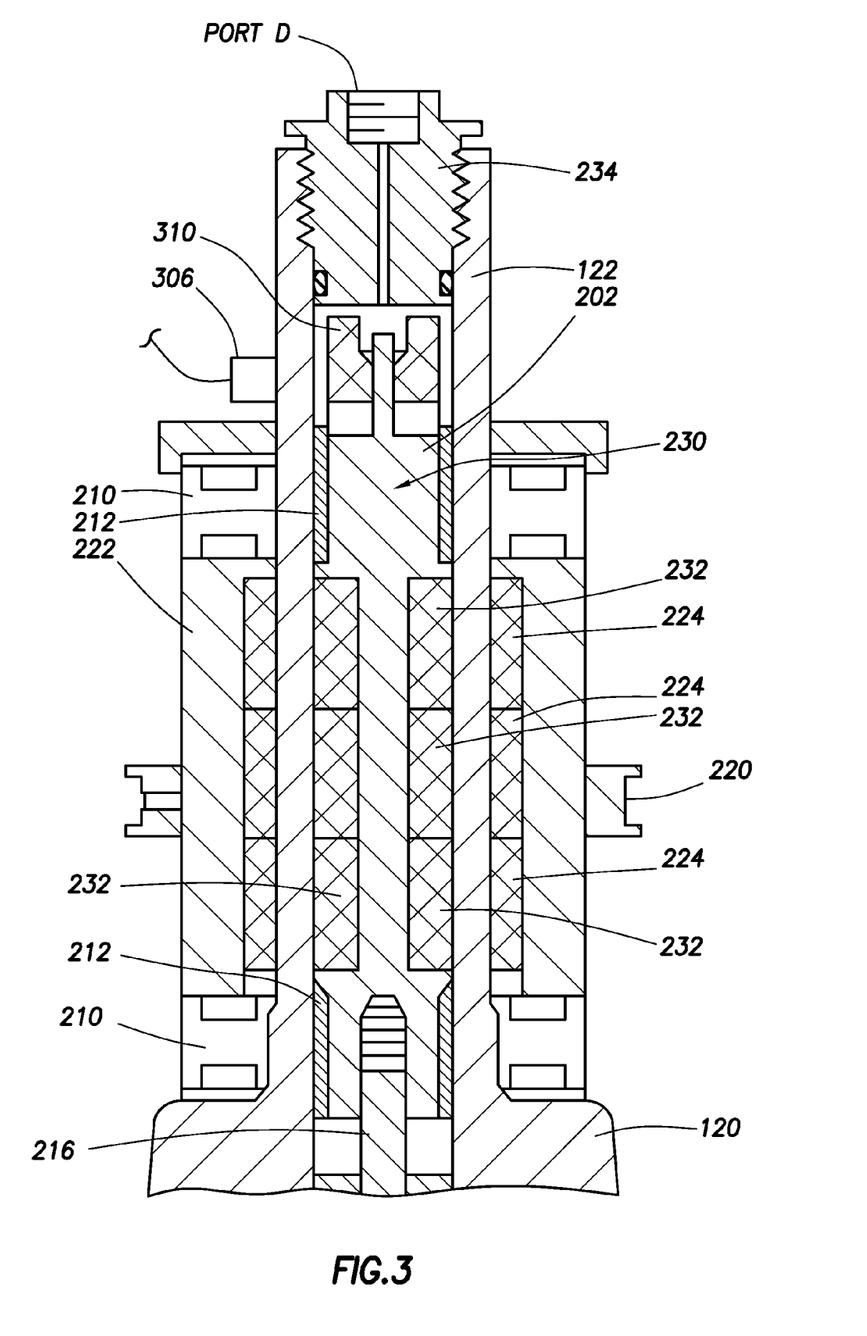
FIG. 3 is an enlarged partial section of the drive section of the FIG. 2 embodiment of the testing apparatus of the present invention.

The magnetic drive assembly 200 is illustrated in detail in FIG. 3. The magnetic drive assembly 200 serves the purpose of transmitting rotational motion via the shaft assembly 202 to the rotating sample contacting paddle assembly 502. The use of magnetic forces through the wall of the housing to drive the rotating paddle assembly 502 is preferred because it eliminates the necessity of having a sealed shaft extending through the wall of the housing. The variations in frictional drag caused by packing or seals around a shaft can cause errors in the readings.

In the FIG. 3 embodiment, a pulley or sheave 220 is connected through an endless belt or chain to a variable speed motor 206 (illustrated in FIG. 1). The sheave 220 is connected to the external magnetic drive housing 222 by a press fit connection or set screws. Magnetic drive housing 222 encloses a plurality of external magnets 224. Bearings 210 rotatably mount the magnetic drive housing 222 around the neck portion 122 of upper subassembly 120. The upper assembly 120 or at least the neck portion 122 is made out of a material with magnetic permeability very close to 1, like Inconel, A-286 or MP35N. This is to ensure that the part 120 transmits all the magnetic flux line for effective coupling but, does not get magnetized during operations. As previously pointed out, the sheave 220 is coupled by an endless belt (not shown in FIG. 3) to a variable speed motor 206. By energizing the motor, the magnetic drive housing 222 and external magnets 224 are rotated about a vertical axis extending through the center of the neck portion 122.

In FIG. 3, the upper end of the shaft assembly 202 is illustrated as comprising a mandrel 230 constructed preferably of strong ferromagnetic materials like 17-4 PH stainless steel. Suitable bearings 212 in the form of cylindrical bushings are provided to mount the mandrel 230 for rotation about a vertical axis extending along the center of the neck portion 122. A plurality of internal magnets 232 are mounted to rotate with the mandrel 230 and are axially positioned adjacent to the external magnets 224. Internal magnets 232 are magnetically coupled to rotate with the external magnets 224. A top plug assembly 234 closes off the upper end of the neck portion 122. In order to remove trapped gases or air, Port D is provided to extend through the top plug assembly 234.

Figure 4:
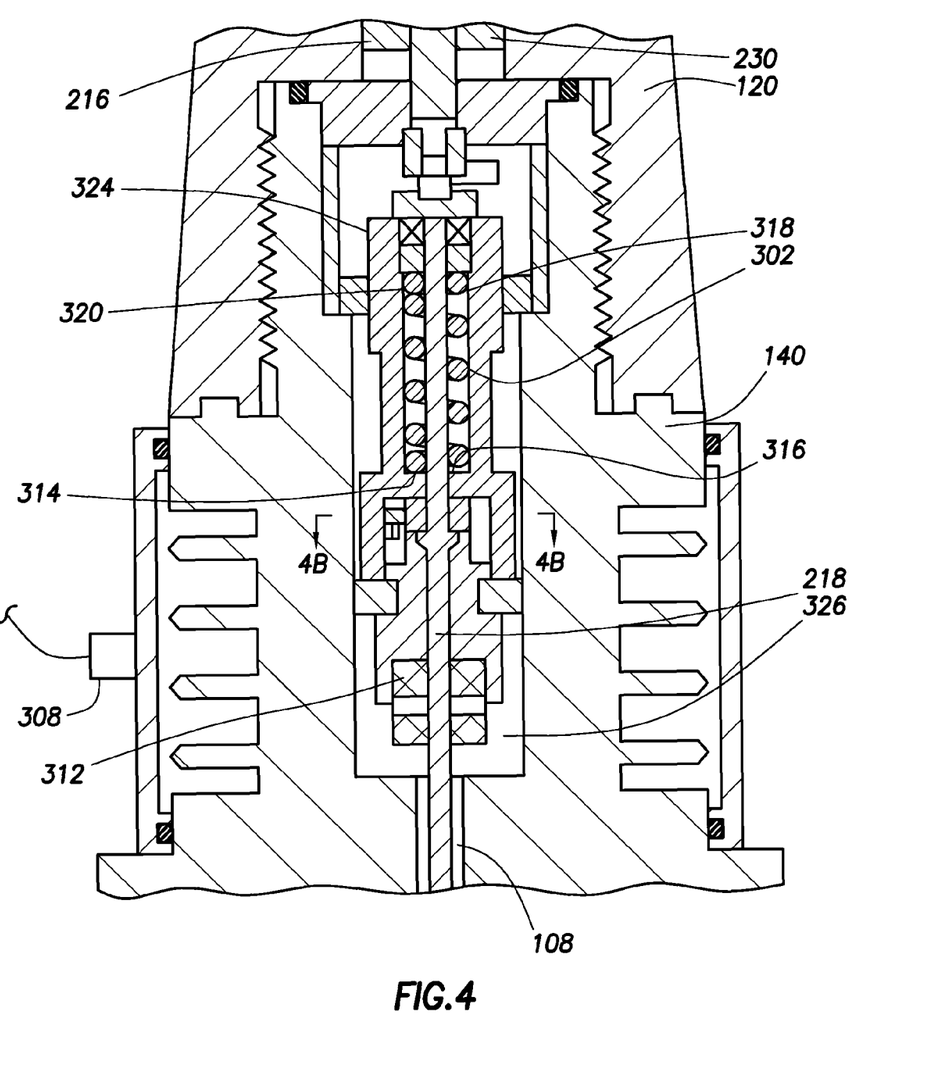
FIG. 4 is an enlarged partial section of the FIG. 2 embodiment of the torsion sensing section of the testing apparatus of the present invention.
Figure 4B:
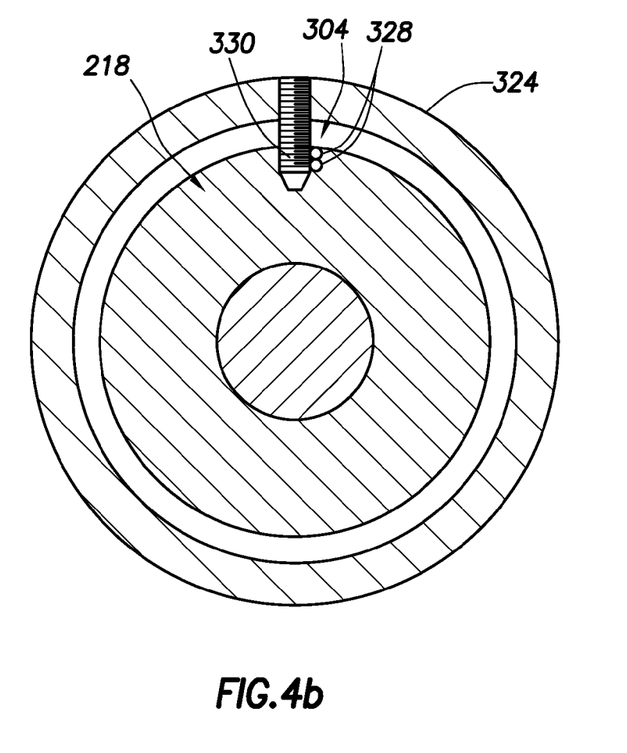
FIG. 4b is an enlarged sectional view taken in FIG. 4 looking in the direction of the arrows of the spring stop of the torsion sensing section of the testing apparatus of the present invention.

The torque spring assembly 300 is illustrated in detail in FIGS. 4 and 4b. Basically, in the torque spring assembly 300, the driven portion of the shaft assembly (mandrel 230) is coupled by a torsion spring 302 to the shaft lower portion 218 of the shaft assembly. Housing 324 is connected to rotate with the mandrel 230. The upper end 318 of the torsion spring 302 is connected at connection 320 to housing 324. The lower end 314 of the torsion spring 302 is connected at 316 to the shaft lower portion 218. It will be appreciated that torque is transferred from the motor to the shaft lower portion 218 through the torsion spring 302. The more resistance to rotation encountered by the sample contacting rotating paddle assembly 502 the more the torsion spring 302 is deformed. This deformation allows the shaft lower portion 218 to rotate with respect to the housing 324.

In FIG. 4b, a spring stop assembly 304 is illustrated in detail for limiting relative rotation between upper mandrel 230 and shaft lower portion 218. In this figure the torsion spring 302 is mounted so that the spring 302 tightens to urge the shaft lower portion 218 in a counterclockwise direction. In this embodiment, the spring stop comprises a pair of vertically extending pins 328 mounted to rotate with the shaft lower portion 218 and a horizontally extending removable set screw 330 mounted to rotate with the mandrel 230. The pins and set screw are positioned to engage when the spring is deflected sufficiently to rotate the set screw and mandrel counterclockwise direction. Interference contact between the pins and screw limit relative rotation. As illustrated, the stop assembly 304 allows about 300° of rotation between the mandrel 230 and the shaft lower portion 218.

Magnets 310 and 312 are mounted on the mandrel 220 (FIG. 3) and shaft lower portion 218 (FIG. 4), respectively. A transducer 306 is illustrated, mounted outside the wall of the top neck portion 122, adjacent to the magnet 310. The transducer 306 senses the rotation of the magnet 310. A second transducer 308 is mounted to sense rotation of the magnet 312. From the relative position of these two magnets the torque in the shaft can be determined. It should be understood that transducers 308 and 310 could be mounted internally rather than externally as illustrated.

Figure 5:
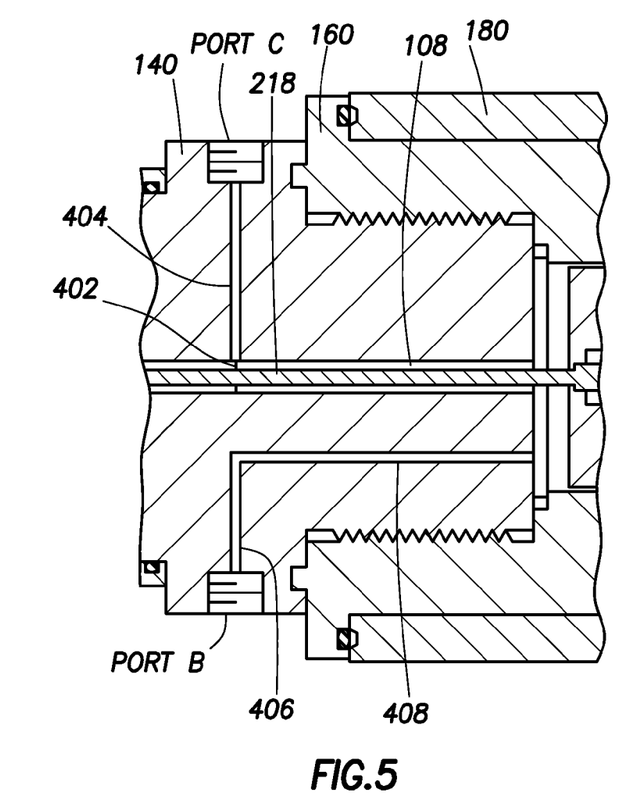
FIG. 5 is an enlarged partial section of the FIG. 2 embodiment of the fluid interface section of the testing apparatus of the present invention.
Figure 5B:
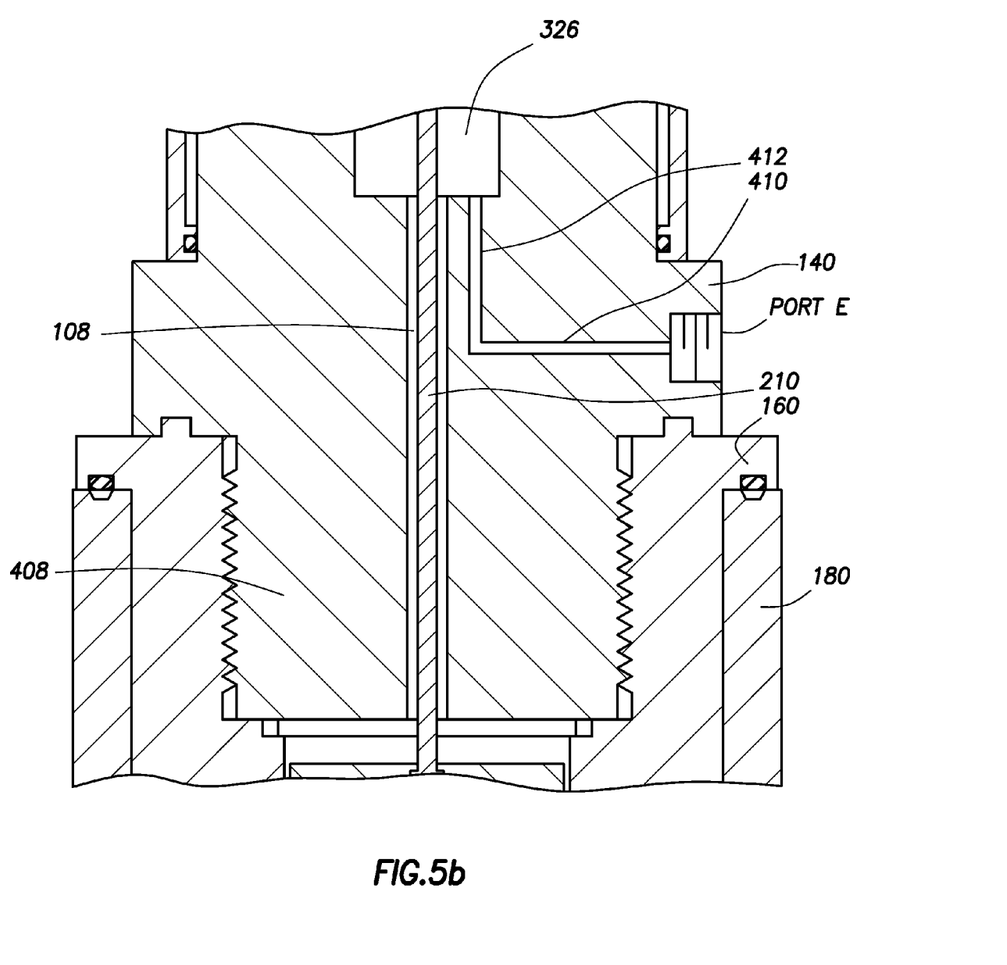
FIG. 5b is a partial section taken at right angle to the section of FIG. 5 showing the fluid interface section of the testing apparatus of the present invention.

The fluid interface assembly 400 is illustrated in detail in FIG. 5. The shaft lower portion 218 is illustrated extending through the passageway 108 in the middle subassembly 140 and into the lower chamber portion 106. The passageway has a substantially reduced cross-section area as compared to the cross sections of the upper and lower chambers. In the illustrated example, passageway 108 is 4.5" long and has a circular cross section shape and is 5/16 inches in diameter. The shaft lower portion 218 extending through passageway 108 has a circular cross section and is 5/32 inches in diameter. This leaves an annular diametrical clearance of 5/32 inches or 0.057 square inches. The annular clearance is selected to be larger than at least four times the size of the largest solid particle to be tested to prevent clogging of the passageway. For example, if proppant is being tested the clearance needs to be larger than particles from 8 to 100 mesh. The length of the passageway and the small annular clearance combine to prevent fluid mixing between the upper and lower chamber portions at the interface as fluids and slurries are tested and added to and withdrawn from the lower chamber portion 106. Preferably, the passageway has a length that is at least about equal to or greater than the maximum cross-section dimension of the passageway, which maximum cross-section dimension, for example, is the diameter in a circular cross-section passageway and the diagonal in a square cross-section passageway.

As illustrated in FIG. 5, Ports B and C are aligned at about the same vertical fluid levels. When fluid is pumped into the lower chamber 106, the fluid will reach and be discharged from open Ports B and C simultaneously. Although this is a preferable configuration, it is important that Port C be located at or above the height of Port B. An internal drilling 404 in middle subassembly 140 connects Port C to the passageway 108. It is preferable that the internal drilling 404 intersect the passageway 108 at about its center so that the fluid interface 402 can move up or down without leaving the passageway. A pair of internal drillings 406 and 408 connects Port B to the lower chamber portion 106. Port E is illustrated in FIG. 5b located at the same vertical level as Ports B and C. However, Port E could be at a different vertical level. Internal drillings 410 and 412 connect Port E to the chamber 326 in middle subassembly 140 at a level preferably above the fluid interface 402. Port E could, of course, be connected to passageway 108 at a location vertically above the fluid interface 402.

Figure 6:
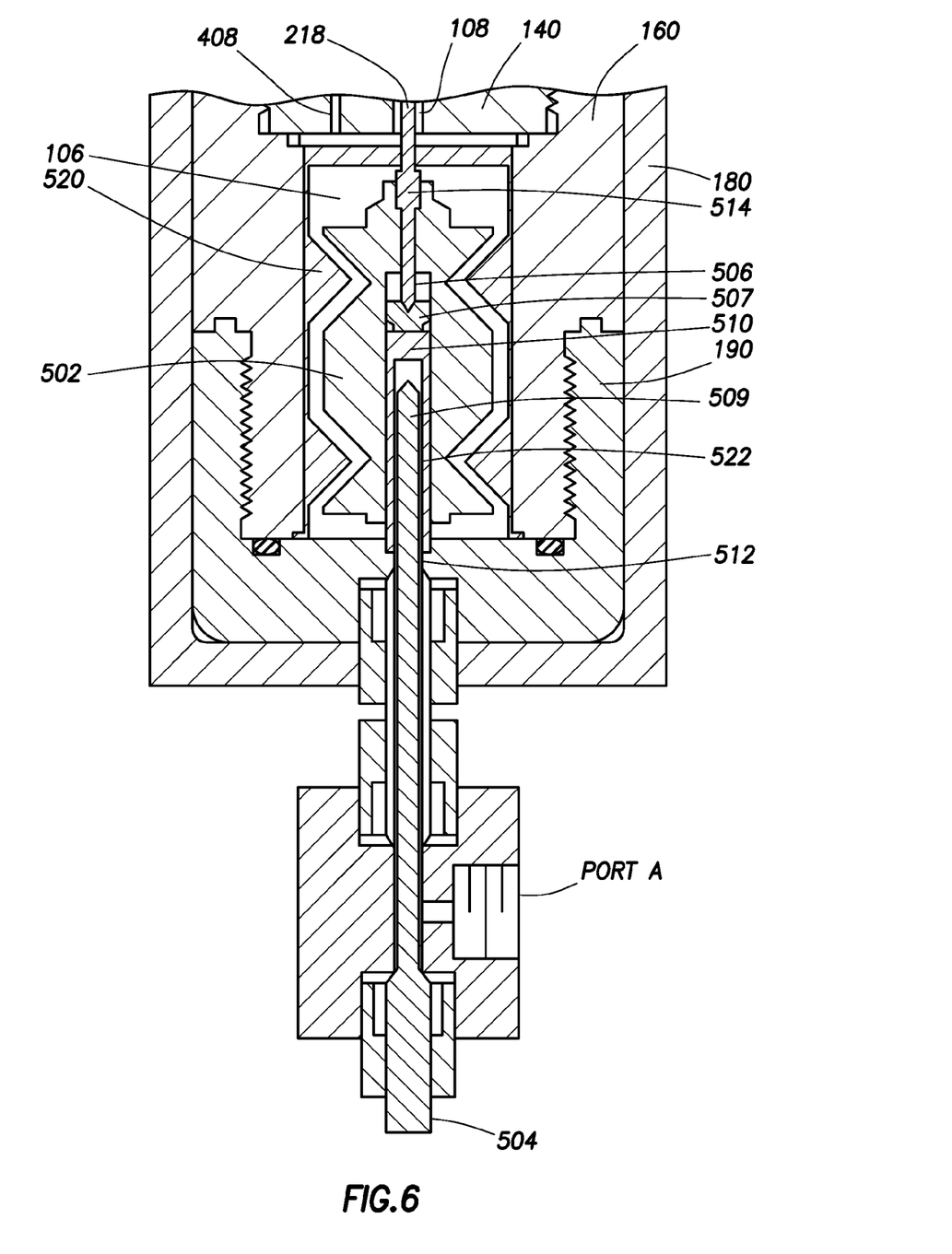
FIG. 6 is an enlarged partial section of the FIG. 2 embodiment of the sample testing section of the testing apparatus of the present invention.

The hot well or sample testing assembly 500 is illustrated in FIG. 6. As can be seen, the shaft's lower portion 218 extends out of the passageway 108 and into rotating paddle assembly 502. Shaft lower end 506 contacts and is supported by bearing 507 supported by tubular member 510. As used herein the term "bearing" is used generically to refer to a device that supports a rotating or sliding part and/or reduces friction—without regard to particular structure of the device and whether the device is a roller, needle or ball bearing, a bushing type bearing, a pivot point contact bearing or the like. Tubular member 510 forms a chamber 522 which is in fluid communication with the lower chamber portion 106. The tubular member 510 is mounted to extend upward from internal bottom cap 190. An opening or passageway 512 extends to the lower center of internal bottom cap 190.

Figure 7:
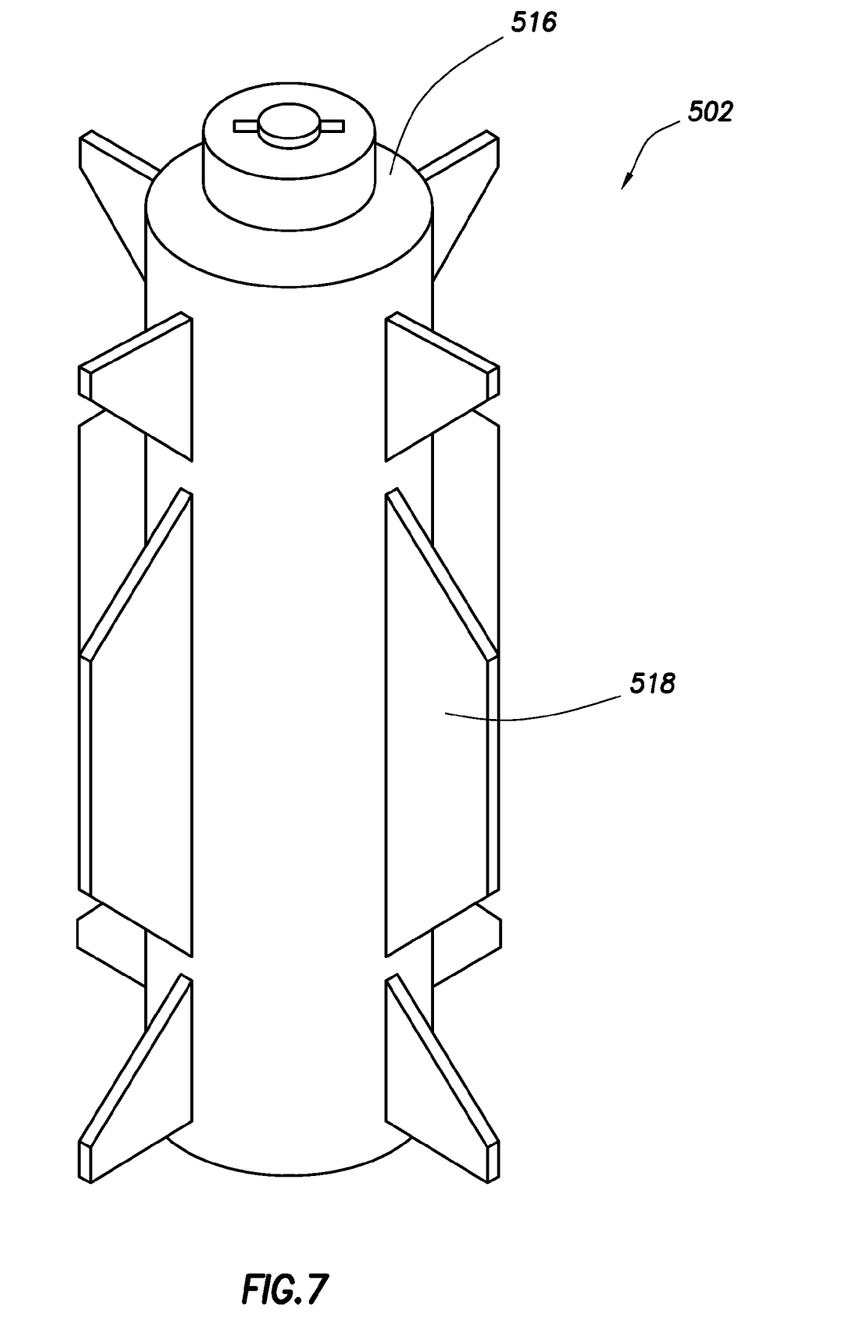
FIG. 7 is a perspective view of the FIG. 2 embodiment of the paddle assembly of the present invention.

As illustrated, shaft lower end 506 has a pair of radially extending shaft flanges 514 which engaged slots in the rotating paddle assembly 502 to couple the rotating paddle assembly 502 to rotate with the shaft lower portion 218. Alternatively, a set screw could be used to couple the rotating paddle assembly to rotate with the shaft. The rotating paddle assembly 502 shown in detail in FIG. 7 is having a cylindrical body 516 with a plurality of radially extending blades 518. As shown in FIG. 6 a plurality of complementary vanes 520 is mounted in the lower chamber portion 106. While the blades and vanes are illustrated having straight edges, it should be appreciated that the terms "paddle" and "blades" used to indicate the sample contacting portion of the apparatus are defined to include other shapes than those illustrated such as cylindrical or frustoconical shapes and those shown in U.S. Pat. Nos. 6,874,353, 6,782,735 and 7,392,842, which are incorporated herein for all purposes.

In the FIG. 6 embodiment, paddle assembly 502 is removably connected to the shaft 218 for ease in cleaning. In addition, vanes 520 are removable for the same reason.

In operation, as the paddle assembly 502 is rotated by the lower shaft portion 218, the paddle will contact the fluid located inside the hot well or sample testing assembly 500. As the paddle rotates, contact with the fluid will apply a torque to the lower shaft portion 218 of the shaft assembly 202. The magnitude of this torque can be measured by the torque spring assembly 300 from which the characteristics of the fluid being tested can be determined.

Also, as shown in FIG. 6, external Port A is connected to passageway 512 and the chamber 522 formed inside of tubular member 510. Tubular Member 510 is opened to lower chamber portion 106 at the lowest level to effectively displace the existing fluid. Port A can be used to add fluids to the lower chamber portion 106. In addition, a temperature sensing assembly 504, such as, a thermocouple assembly 509, is mounted as shown with its temperature sensing probe located inside the chamber 522 in contact with the fluid in the lower chamber portion 106.

While compositions and methods are described in terms of "comprising," "containing," or "including" various components or steps, the compositions and methods also can "consist essentially of" or "consist of" the various components and steps. As used herein, the words "comprise," "have," "include," and all grammatical variations thereof are each intended to have an open, non-limiting meaning that does not exclude additional elements or steps.

Therefore, the present inventions are well adapted to carry out the objects and attain the ends and advantages mentioned as well as those which are inherent therein. While the invention has been depicted, described, and is defined by reference to exemplary embodiments of the inventions, such a reference does not imply a limitation on the inventions, and no such limitation is to be inferred. The inventions are capable of considerable modification, alteration, and equivalents in form and function, as will occur to those ordinarily skilled in the pertinent arts and having the benefit of this disclosure. The depicted and described embodiments of the inventions are exemplary only, and are not exhaustive of the scope of the inventions. Consequently, the inventions are intended to be limited only by the spirit and scope of the appended claims, giving full cognizance to equivalents in all respects.

Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A method of measuring the shear stress of a test liquid at an elevated test pressure, the method comprising the steps of:
   placing the test liquid in the internal chamber of a container;
   selecting a second liquid which is immiscible in the test liquid;
   placing the second liquid in the chamber in contact with the test liquid to form a liquid interface between the test liquid and second liquid;
   positioning a shaft to extend between the first and second liquids and through the liquid interface, the shaft having a test liquid contacting member on the one end positioned to be in contact with the test liquid;
   selecting a test pressure different from 1 atmosphere and bringing the test liquid to the test pressure;
   while the test liquid is at the test pressure, rotating the shaft to move the member in the test fluid while determining the relative viscosity of the test liquid by measuring the drag created by the movement of the member; and
   additionally comprising replacing at least a portion of the test liquid with a second and different test liquid while maintaining the liquid interface in the reduced cross section area, mixing the test liquids and thereafter determining relative viscosity of the mixture of test liquids at test pressure above atmospheric pressure.

2. The method according to claim 1, wherein the replacing step is performed while maintaining the liquids in the chamber at a pressure greater than atmospheric.

3. The method according to claim 1, wherein the step of rotating the shaft is performed at the test temperature.

4. The method according to claim 1, wherein the step of rotating the shaft comprises magnetically coupling the shaft to a motor and operating the motor.

5. The method according to claim 1, wherein the step of moving the member comprises rotating a paddle.

6. The method according to claim 1, wherein the step of measuring the drag created by moving the member comprises measuring the torque in the shaft.

7. The method according to claim 6, wherein the step of measuring the torque in the shaft comprises deflecting a spring and measuring the deflection in the spring.

8. The method according to claim 1, wherein the step of forming a liquid interface between the test liquid and second liquid comprises maintaining a liquid interface while performing the shaft rotation step.

9. The method according to claim 8, additionally comprising the step of maintaining the liquid interface in a reduced cross section area while performing the shaft rotation step.

10. The method according to claim 9, wherein the reduced cross section area is a passageway.

11. A method of measuring the shear stress of a test liquid at an elevated test pressure, the method comprising the steps of:
   placing the test liquid in the internal chamber of a container;
   selecting a second liquid which is immiscible in the test liquid;
   placing the second liquid in the chamber in contact with the test liquid to form a liquid interface between the test liquid and second liquid;
   positioning a shaft to extend between the first and second liquids and through the liquid interface, the shaft having a test liquid contacting member on the one end positioned to be in contact with the test liquid;
   selecting a test pressure different from 1 atmosphere and bringing the test liquid to the test pressure;
   while the test liquid is at the test pressure, rotating the shaft to move the member in the test fluid while determining the relative viscosity of the test liquid by measuring the drag created by the movement of the member; and
   testing the relative viscosity of the test liquid while flowing test liquids through the chamber while maintaining the liquid interface in the reduced cross section area.

12. A method of measuring the shear stress of a test liquid at an elevated test pressure, the method comprising the steps of:
   placing the test liquid in the internal chamber of a container;
   selecting a second liquid which is immiscible in the test liquid;
   placing the second liquid in the chamber in contact with the test liquid to form a liquid interface between the test liquid and second liquid;
   positioning a shaft to extend between the first and second liquids and through the liquid interface, the shaft having a test liquid contacting member on the one end positioned to be in contact with the test liquid;
   selecting a test pressure different from 1 atmosphere and bringing the test liquid to the test pressure;
   while the test liquid is at the test pressure, rotating the shaft to move the member in the test fluid while determining the relative viscosity of the test liquid by measuring the drag created by the movement of the member; and
   wherein test liquid is flowed through the chamber while the step of moving the shaft is performed.

13. A method of measuring the shear stress of a test liquid at an elevated test pressure, the method comprising the steps of:
   placing the test liquid in the internal chamber of a container; selecting a second liquid which is immiscible in the test liquid;
   placing the second liquid in the chamber in contact with the test liquid to form a liquid interface between the test liquid and second liquid, wherein the reduced cross section area is a passageway and the passageway has a length to maximum cross section dimension ratio of at least about one or greater;
   positioning a shaft to extend between the first and second liquids and through the liquid interface, the shaft having a test liquid contacting member on the one end positioned to be in contact with the test liquid; selecting a test pressure different from 1 atmosphere and bringing the test liquid to the test pressure; and
   while the test liquid is at the test pressure and while the fluid interface is maintained in the reduced cross section passageway, rotating the shaft to move the member in the test fluid while determining the relative viscosity of the test liquid by measuring the drag created by the movement of the member; and
   the passageway has a length to maximum cross section dimension ratio of at least about one or greater.

14. A fluid testing apparatus comprising:
a housing comprising first and second enclosed chambers;
a portion separating the first and second chambers and forming a reduced cross section passageway connecting the first and second chambers in fluid communication with each other, and, wherein the passageway has a length to maximum cross section dimension ratio of at least about one or greater;
a first fluid in the first chamber and a second fluid in the second chamber; a fluid interface between the first and second fluids located in the reduced cross section;
an axially rotatable shaft in the housing, extending between the first and second chambers and through the reduced cross section and fluid interface; and
a member contacting the second fluid in the second chamber, the member connected to move with the shaft; and
the passageway has a length to maximum cross section dimension ratio of at least about one or greater.

15. The apparatus according to claim 14 wherein the reduced cross section portion has a maximum cross-section area which is less than the maximum cross-section area of the first and second chambers.

16. The testing apparatus according to claim 14 additionally comprising a motor magnetically coupled to the shaft to selectively rotate the shaft.

17. The testing apparatus according to claim 14 additionally comprising means for sensing torsion in the shaft.

18. A fluid testing apparatus comprising:
a housing comprising first and second enclosed chambers;
a portion separating the first and second chambers and forming a reduced cross section connecting the first and second chambers in fluid communication with each other;
a first fluid in the first chamber and a second fluid in the second chamber; a fluid interface between the between the first and second fluids located in the reduced cross section;
an axially rotatable shaft in the housing extending between the first and second chambers and through the reduced cross section and fluid interface, the shaft comprises first and second relatively rotatable portions and additionally comprising a spring located in the first fluid, the spring connected between the first and second shaft portions; and
a member contacting the second fluid in the second chamber, the member connected to move with the shaft.

* * * * *